United States Patent [19]

Sauveur

[11] Patent Number: 4,820,155
[45] Date of Patent: Apr. 11, 1989

[54] DAM FRAME FOR USE DURING ENDODONTIC SURGERY

[76] Inventor: Marie-Joseph G. Sauveur, 26, Rue du Four, 91540 Ormoy, France

[21] Appl. No.: 84,388

[22] Filed: Aug. 11, 1987

[30] Foreign Application Priority Data

Aug. 13, 1986 [FR] France .................. 86 11689

[51] Int. Cl.⁴ ............................................. A61C 5/14
[52] U.S. Cl. ............................................ 433/136
[58] Field of Search ............................. 433/136, 137

[56] References Cited

U.S. PATENT DOCUMENTS 3,772,790 11/1973 Swan-Gett et al. ............... 433/136
4,600,387 7/1986 Ross .................................. 433/136

Primary Examiner—Carroll B. Dority, Jr.
Attorney, Agent, or Firm—Wolf, Greenfield & Sacks

[57] ABSTRACT

The invention relates to a dam frame for creating an operative field during endodontic surgery. The dam frame has at least two frame members connected by hinges to form a closed loop. The dam frame supports a rubber membrane. The frame members may be folded in relation to one another to provide easy access to the buccal cavity while maintaining the aseptic conditions surrounding the tooth or teeth isolated by the dam.

4 Claims, 3 Drawing Sheets

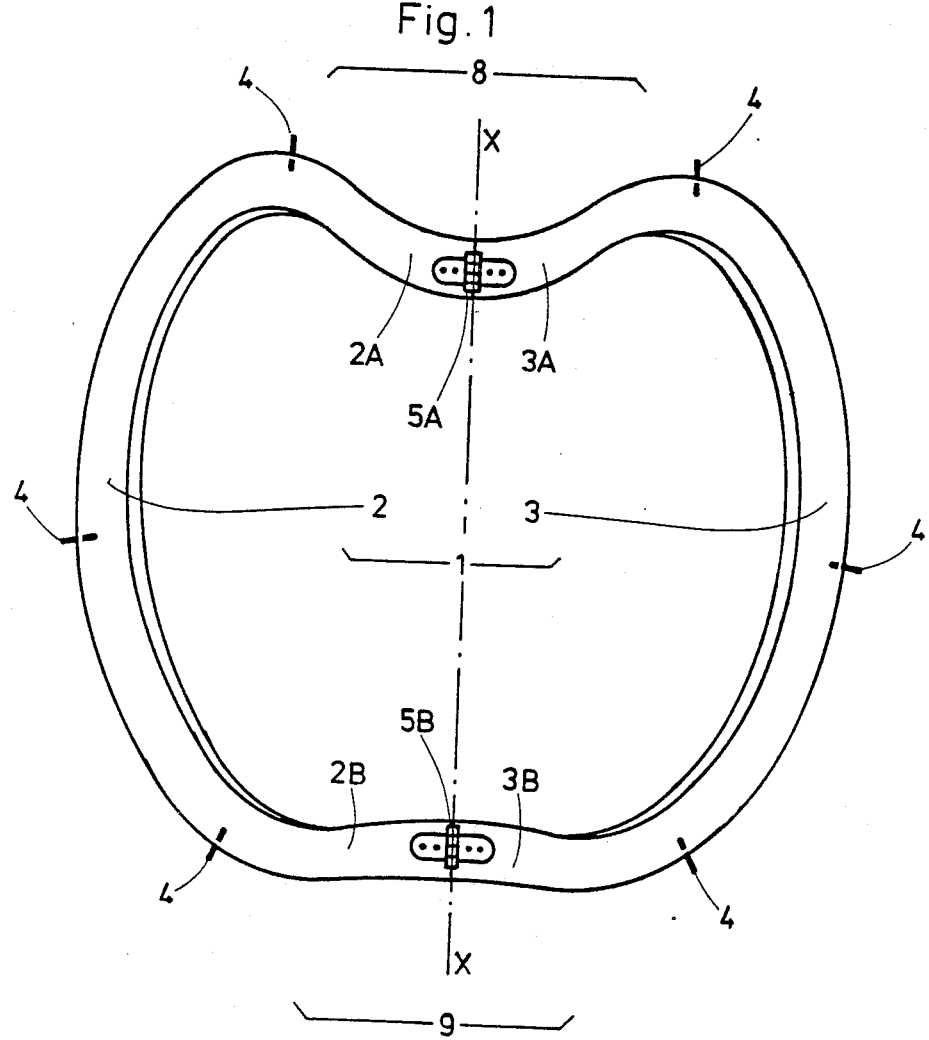

Fig. 4
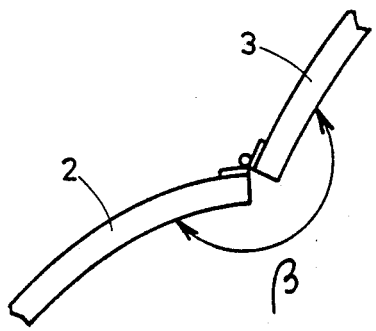
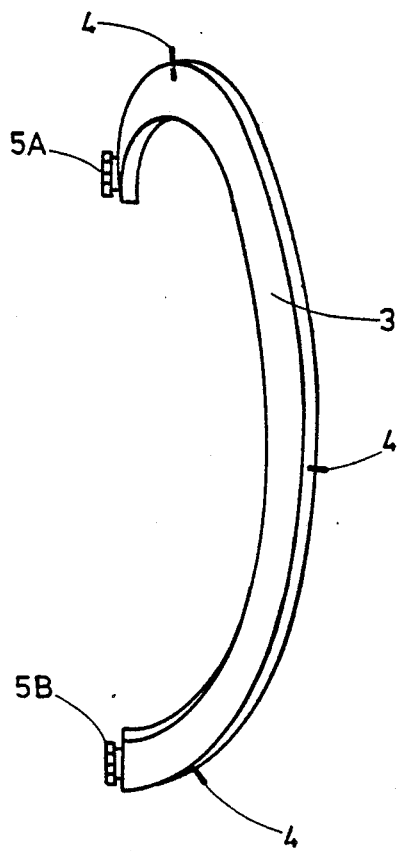
Fig. 3

DAM FRAME FOR USE DURING ENDODONTIC SURGERY

The present invention relates to an operative field for endodontic surgery, the said field being composed of a frame and a sheet of rubber or dam adapted to be positioned around the tooth or group of teeth to be treated and stretched over the frame.

This operative field is intended particularly to protect the patient from swallowing small endodontic instruments, to retain the products of introcanalicular irrigation, to maintain dryness at the operative site by avoiding contamination thereof by saliva, and to keep the soft tissues such as the cheeks and tongue away from the site.

There are various types of disc frames such as, for example, those described in the clinical endodontics guide of R. Bence (Editions Lucien Prelat). Among the rubber-dams and in particular the frames mentioned in this document, there is the U-shaped frame of Young, which is of metal, the Star Visi frame or the Nygard-Ostby frame which are of synthetic plastics material. It is, furthermore, preferable for the frames to be of synthetic plastics material in order to avoid their interference with X-rays.

Although operative fields may be of considerable interest for the reasons mentioned above, they do have the not inconsiderable disadvantage of complicating X-ray photography.

Well, the operative field is used for endodontic treatments, that is to say the occlusion of the intraradicular channels of a tooth and such operations which must be particularly meticulous, do require the operation to be monitored by the taking of successive X-ray plates to verify the evolution of the work of occluding the intraradicular channels.

By reason of the presence of the dam, access to the buccal cavity behind the dam and the taking of X-ray photographs are particularly difficult because the frame has to be more or less lifted by pulling on the rubber membrane, at the risk of moving it away from the tooth and of being obliged to refit it in a particularly delicate fashion.

Furthermore, if the frame cannot be lifted sufficiently, positioning of the photographic film becomes very tricky and, above all, such positioning cannot be carried out sufficiently accurately in the case of repetitive photographs intended to monitor the progress of the work.

The object of the present invention is to create an operative field which combines the main advantages of the rubber-dam, in other words aseptic conditions, and the prevention of the patient inhaling and swallowing materials and/or endodontic instruments, while at the same time facilitating and allowing X-ray photographs to be taken under the very best conditions of accuracy and of repetition of photographs.

To this end, the invention relates to an operative field of the type mentioned hereinabove, characterised in that the frame consists of at least two parts connected by an articulating means by which one part can be at least partially folded over in relation to the other.

Thus, according to the invention, the operative field may effectively play its part while facilitating access to the buccal cavity, providing the necessary visibility and permitting positioning of the X-ray plate under satisfactory conditions of precision, permitting monitoring of the endodontic operation.

According to an advantageous characteristic feature, the articulating means consists of at least one hinge connecting the two parts of the frame.

However, it may likewise be envisaged to produce the frame from synthetic material, integrating the hinge or hinges into this frame, for example by reducing the thickness of the material in order to form an articulating means which employs as a hinge the natural elasticity of the material.

In a particularly advantageous manner, the frame is closed. It is of symmetrical form in relation to its articulating means and has a concave part at the level of the nose. This permits of better positioning of the frame of the dam not only so that it can be applied against the face of the patient but also in order to take into account the subdivision of the buccal cavity into four parts (upper jaw; left and right-hand parts; lower jaw: left and right-hand parts).

In a particularly advantageous manner, the frame is of three-dimensional dished form, matching the facial curvature of an individual at the level of his buccal cavity and the axis of articulation which is situated in the median plane passes through the summit of the dished portion.

According to another important characteristic feature, the articulating means between the two parts opens only in one direction. This means that when the frame of the dam is placed around the buccal cavity and occupies its shape surrounding this buccal cavity, the articulating means are in abutment, the elasticity of the rubber wheel constituting the dam pulling on the frame so that it keeps its shape.

On the other hand, the articulating means may open in the other semi-plane, that is to say the articulating means makes it possible to raise one of the parts of the frame which may not be occupied by the tooth or teeth involved in the endodontic operation for examination of the buccal cavity and above all in order to place an x-ray film in position.

The present invention will be described in greater details with reference to the appended drawings, in which:

FIG. 1 is a front view of a dam frame according to the invention;

FIG. 2 is a view of the dam frame shown in FIG. 1, from below;

FIG. 3 is a side view of the dam frame shown in FIG. 1, and

FIG. 4 is a plan view of FIG. 3.

Figure 5:
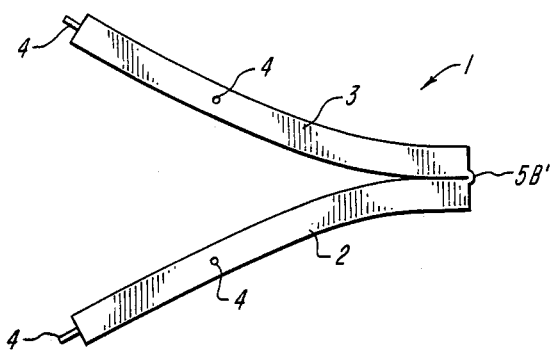
FIGS. 5 and 6 are views of a further embodiment of a dam frame in open and closed positions.

In accordance with FIGS. 1 and 2, the invention relates to an operative field for endodontic surgery. This field consists of a frame 1 of two parts 2, 3, and carrying barbs 4 distributed around the periphery of the frame and on which the rubber sheet or dam is hooked, being provided with a hole and which has been previously fitted over the tooth to be treated.

The two parts 2, 3 of the frame are connected at the level of their ends 2a, 3a, 2b, 3b, be a respective articulating means 5a, 5b. These two articulating means are preferably aligned on one and the same axis X—X. However, as the material and the structure of the frame 1 imparts a certain elasticity thereto, it is not essential for the axes of articulating means 5a, 5b to be strictly aligned.

In certain cases, according to the shape of the frame, it may even by of interest not to have these two axes aligned (while keeping them if necessary in the plane of symmetry of the frame) in order to create or accentuate a metastable position effect between a position of opening (such as that shown in FIG. 1) and a position of being folded, when the frame is subject to the tension exerted by the flexible sheet.

Generally speaking, the frame 1 is symmetrical in shape in relation to the plane passing through its axes of articulation X—X. As FIGS. 1, 2, 3 show, this frame is of three-dimensional form, matching the facial curvature of an individual at the level of his buccal cavity. In this case, it is interesting for the axis of articulation to pass through the apex of the dished portion.

As already indicated, the articulating means 5a, 5b open only in one direction. This is clearly evident in FIG. 2.

According to FIG. 2, the two ends 2a, 3a or 2b, 3b of the parts 2 and 3, abut one against the other, locking them at an angle α.

On the other hand, the two parts 2, 3 can pivot one in relation to the other in the opposite direction, as illustrated in FIG. 4, in order to gain access to the buccal cavity.

As shown in FIG. 4, the part 3 has been raised in relation to the part 2 by the opening of the angle of the hinge, according to the angle β. This makes it possible to examine the buccal cavity and above all to position an X-ray film.

Figure 6:
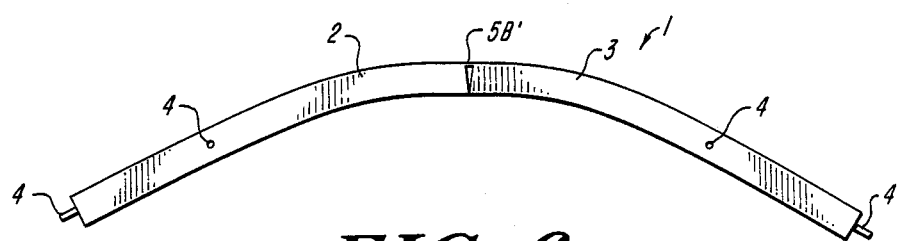

According to an alternative embodiment, the hinges 5A' and 5B' in FIGS. 5 and 6 are made in a single piece with the parts 2 and 3, so that the frame 1 constitutes only one, for example synthetic plastics moulded, assembly, with a subdivision along the axis X—X in order to diminish the thickness of the material and to constitute hinges which utilise the elasticity of the material; the oppositely disposed faces of the ends 2A, 3A and 2B, 3B likewise constitute abutments upon closure of the frame (see FIG. 2).

Generally, the frame which is of slightly elliptical form, and of which the upper part 8 is concave and of which the lower part 9 is flattened, forms at its base a gutter which makes it possible to fold back the flexible sheet in order to collect the irrigation products.

I claim:

1. A dam frame and a sheet of material which is adapted to be positioned around a tooth (or group of teeth) which is or are to be treated and stretched over the frame, characterised in that the frame consists of at least two parts connected by an articulating means comprising two hinges that open only in one direction and which makes it possible at least partially to fold one part over in relation to the other, the frame being a closed loop with a concave part and spaced barbs in its outer periphery 2. Dam frame according to claim 1, characterised in that the articulating means consists of a reduction in the thickness of the frame at the junction of the two parts, the assembly being made in a single piece.

3. Dam frame according to claim 1, characterised in that the frame is of three-dimensional form, being substantially dished in order to match the facial curvature of an individual at the level of his mouth, the axis of articulation passing through the apex of the dished part.

4. A dam frame according to claim 1, characterised in that the frame is symmetrical in relation to the articulating means.

* * * * *